(12) United States Patent
Campbell et al.

(10) Patent No.: US 11,995,201 B2
(45) Date of Patent: May 28, 2024

(54) HEADPHONES WITH TIMING CAPABILITY AND ENHANCED SECURITY

(71) Applicant: NURA HOLDINGS PTY LTD, Brunswick (AU)

(72) Inventors: Luke John Campbell, Brunswick (AU); Dragan Petrovic, Union City, CA (US); David James Lawson, Brunswick (AU)

(73) Assignee: Nura Holdings Pty Ltd, Brunswick (AU)

( * ) Notice: Subject to any disclaimer, the term of this patent is extended or adjusted under 35 U.S.C. 154(b) by 338 days.

(21) Appl. No.: 17/411,934

(22) Filed: Aug. 25, 2021

(65) Prior Publication Data

US 2021/0383011 A1    Dec. 9, 2021

Related U.S. Application Data

(63) Continuation of application No. PCT/US2020/019106, filed on Feb. 20, 2020.

(60) Provisional application No. 62/812,460, filed on Mar. 1, 2019.

(51) Int. Cl.
*G06F 21/62* (2013.01)
*G06F 21/60* (2013.01)
*G06F 21/84* (2013.01)
*H04R 1/10* (2006.01)
*H04R 29/00* (2006.01)

(52) U.S. Cl.
CPC ........ *G06F 21/6218* (2013.01); *G06F 21/602* (2013.01); *G06F 21/84* (2013.01); *H04R 1/1008* (2013.01); *H04R 1/1041* (2013.01); *H04R 29/001* (2013.01)

(58) Field of Classification Search
CPC .... G06F 21/6218; G06F 21/602; G06F 21/84; H04R 1/1008; H04R 1/1041; H04R 29/001
USPC ................................. 381/59, 58, 56
See application file for complete search history.

(56) References Cited

U.S. PATENT DOCUMENTS

| 7,529,370 | B1 | 5/2009 | Zhang et al. |
| 10,051,460 | B2 | 8/2018 | Bran |
| 11,144,646 | B2 | 10/2021 | Maretti et al. |

(Continued)

FOREIGN PATENT DOCUMENTS

| CN | 109 068 205 | 12/2018 |
| WO | WO 2008/087614 | 7/2008 |
| WO | WO 2020/180499 | 9/2020 |

OTHER PUBLICATIONS

International Search Report and Written Opinion dated May 19, 2020 for International Application No. PCT/US2020/019106, filed on Feb. 20, 2020 (13 pages).

*Primary Examiner* — Thjuan K Addy
(74) *Attorney, Agent, or Firm* — Knobbe, Martens, Olson, & Bear, LLP

(57) ABSTRACT

An audio device, such as a headphone, can create, maintain and use secure data. The secure data can include an amount of time that the user has used the audio device and/or an amount of time allocated to the user. When the amount of time the user has used the audio device exceeds the amount of time allocated to the user, the audio device can stop emitting the audio. The secure data can also include a hearing profile of the user, which can uniquely identify the user. The secure data associated with the headphone can be encrypted to prevent tampering.

19 Claims, 7 Drawing Sheets

(56) References Cited

U.S. PATENT DOCUMENTS

| | | |
|---|---|---|
| 2007/0155313 A1 | 7/2007 | Goldberg et al. |
| 2008/0318518 A1 | 12/2008 | Coutinho et al. |
| 2012/0095749 A1 | 4/2012 | Capretta |
| 2012/0159617 A1* | 6/2012 | Wu ............... H04R 1/1041 726/19 |
| 2014/0162556 A1 | 6/2014 | Dua |
| 2018/0124527 A1 | 5/2018 | El-Hoiydi et al. |

* cited by examiner

HEADPHONES WITH TIMING CAPABILITY AND ENHANCED SECURITY

CROSS-REFERENCE TO RELATED APPLICATIONS

This application is a continuation of International Patent Application No. PCT/US2020/019106, filed on Feb. 20, 2020, which claims benefit of priority to the U.S. provisional patent application Ser. No. 62/812,460 filed on Mar. 1, 2019, titled "HEADPHONES WITH TIMING CAPABILITY AND ENHANCED SECURITY," which is incorporated herein by reference in its entirety.

TECHNICAL FIELD

The present application is related to a headphone, and more specifically to methods and systems that provide headphones with timing capability and enhanced security.

BACKGROUND

The functionality of consumer audio devices, such as headphones, are limited due to power and cost concerns. As a result, no secure data can be created, maintained, and/or used by the audio devices because maintenance of the secure data requires additional power and electronic components.

SUMMARY

Presented here is an audio device, such as a headphone, that can create, maintain and use secure data. The secure data can include an amount of time that the user has used the audio device and/or an amount of time allocated to the user. When the amount of time the user has used the audio device exceeds the amount of time allocated to the user, the audio device can stop emitting the audio. The secure data can also include a hearing profile of the user, which ca uniquely identify the user. The secure data associated with the headphone can be encrypted to prevent tampering.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

DETAILED DESCRIPTION

Terminology

Figure 1A:
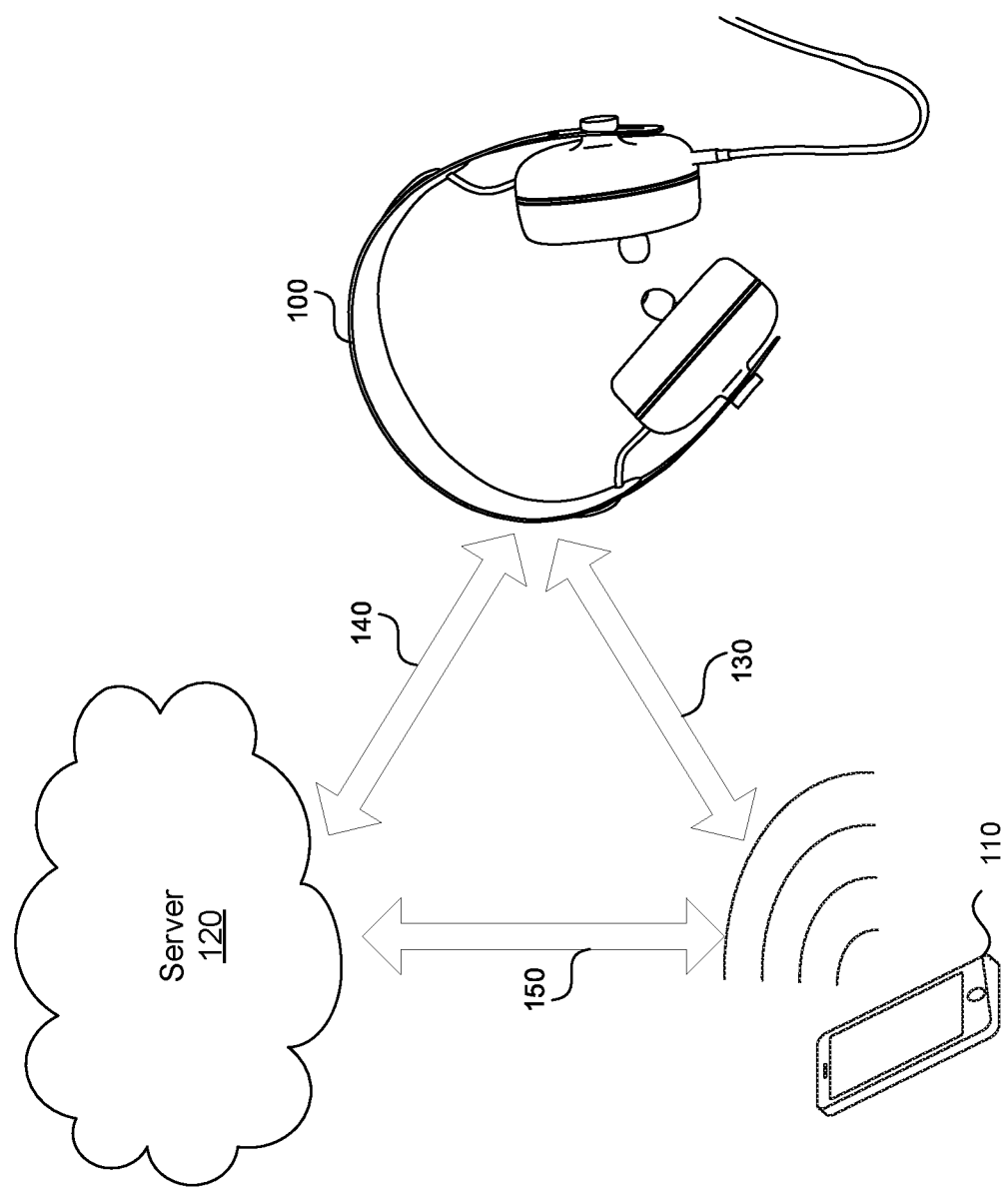
FIGS. 1A-1B shows a system including an audio device with timing capabilities and enhanced security.

Brief definitions of terms, abbreviations, and phrases used throughout this application are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

Headphones with Timing Capability and Enhanced Security

Presented here is an audio device, such as a headphone, that can create, maintain and use secure data. The secure data can include an amount of time that the user has used the audio device and/or an amount of time allocated to the user. When the amount of time the user has used the audio device exceeds the amount of time allocated to the user, the audio device can stop emitting the audio. The secure data can also include a hearing profile of the user, which ca uniquely identify the user. The secure data associated with the audio device can be encrypted to prevent tampering. The audio device can be personal audio device such as a headphone, an earbud, a headset, etc.

The system and methods presented here provide a new interface to an audio device, enhance security of the audio device, and even generate new data associated with a user. The audio devices presented in this application provide a new interface to the user by enabling the user to use the audio device for a predetermined amount of time. The audio device has a timer to measure an amount of time the user uses the audio device, and to prevent the user from using the audio device once the predetermined amount of time has been exceeded. The audio device also has an encryption member which can prevent others from tampering with the predetermined amount of time and other personal information associated with the user. While measuring the amount of time the user has used the audio device, the audio device generates new data by reducing the amount of time allocated to the user or by increasing the usage time counter associated with the user. Further, while the user listens to the audio device, the audio device can create a hearing profile of the user which ca uniquely identify the user. The hearing profile of the user is an example of new data generated while the user is using the audio device. The hearing profile of the user can also be encrypted because the hearing profile ca uniquely identify the user.

Figure 1B:
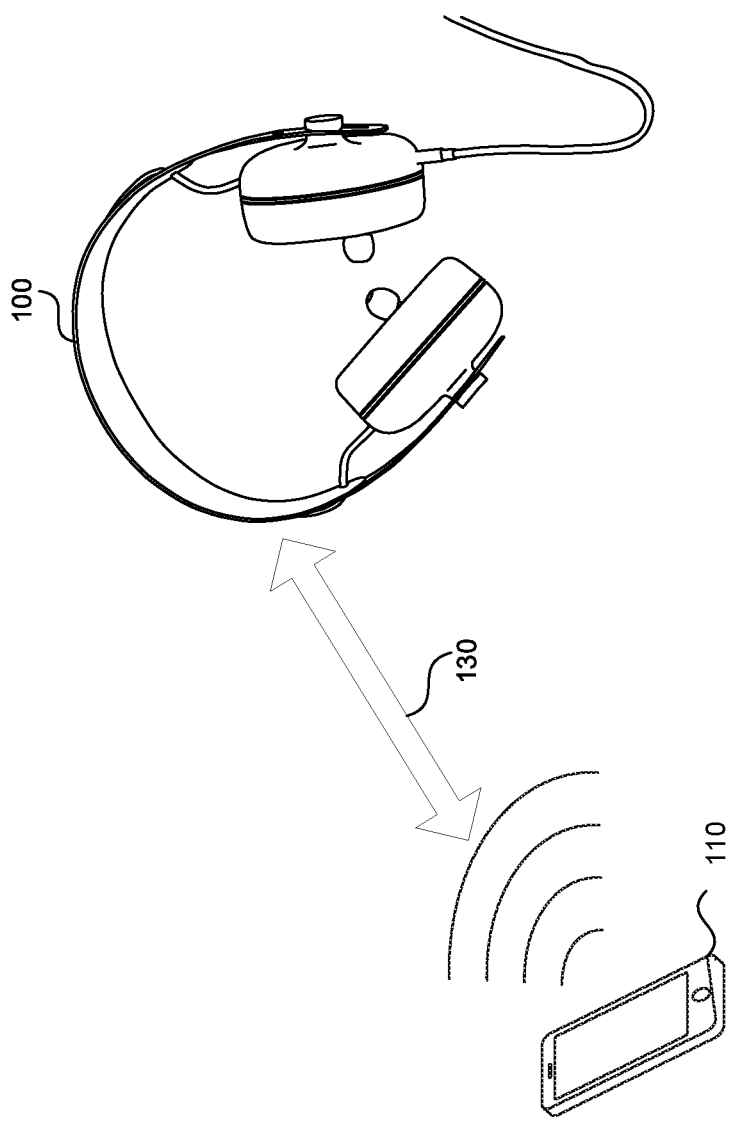

FIGS. 1A-1B show a system including an audio device with timing capabilities and enhanced security. The system includes an audio device 100, a mobile device 110, a server 120 and communication channels 130, 140, 150. In one embodiment shown in FIG. 1B, the server 120 is not needed, and the functions of the server can be performed by either the mobile device 110 or the headphone 100.

The audio device 100 can be a headphone as shown in FIGS. 1A-1B, a hearing aid, an earphone, an earbud, an Air Pod, etc. The mobile device 110 can be a cell phone, a tablet, a personal digital assistant, or any device with a display capable receiving user input. The server 120 can include one or more processors in communication with each other and connected to the Internet. The one or more processors can be associated with a cloud computer.

The communication channel 130 between the mobile device 110 and the headphone 100 can include wired or wireless protocols such as Bluetooth, Wi-Fi, infrared, near field communication, ultraband, Zigbee, etc. The communication channels 140, 150 with the server 120 can utilize the Internet, cellular networks, local area networks, mesh networks, peer-to-peer networks, satellite networks, etc. The communication over communication channels 130, 140, 150 can be encrypted, for example using private-public-key cryptography. The private encryption key can be stored in the headphone 100.

Figure 2:
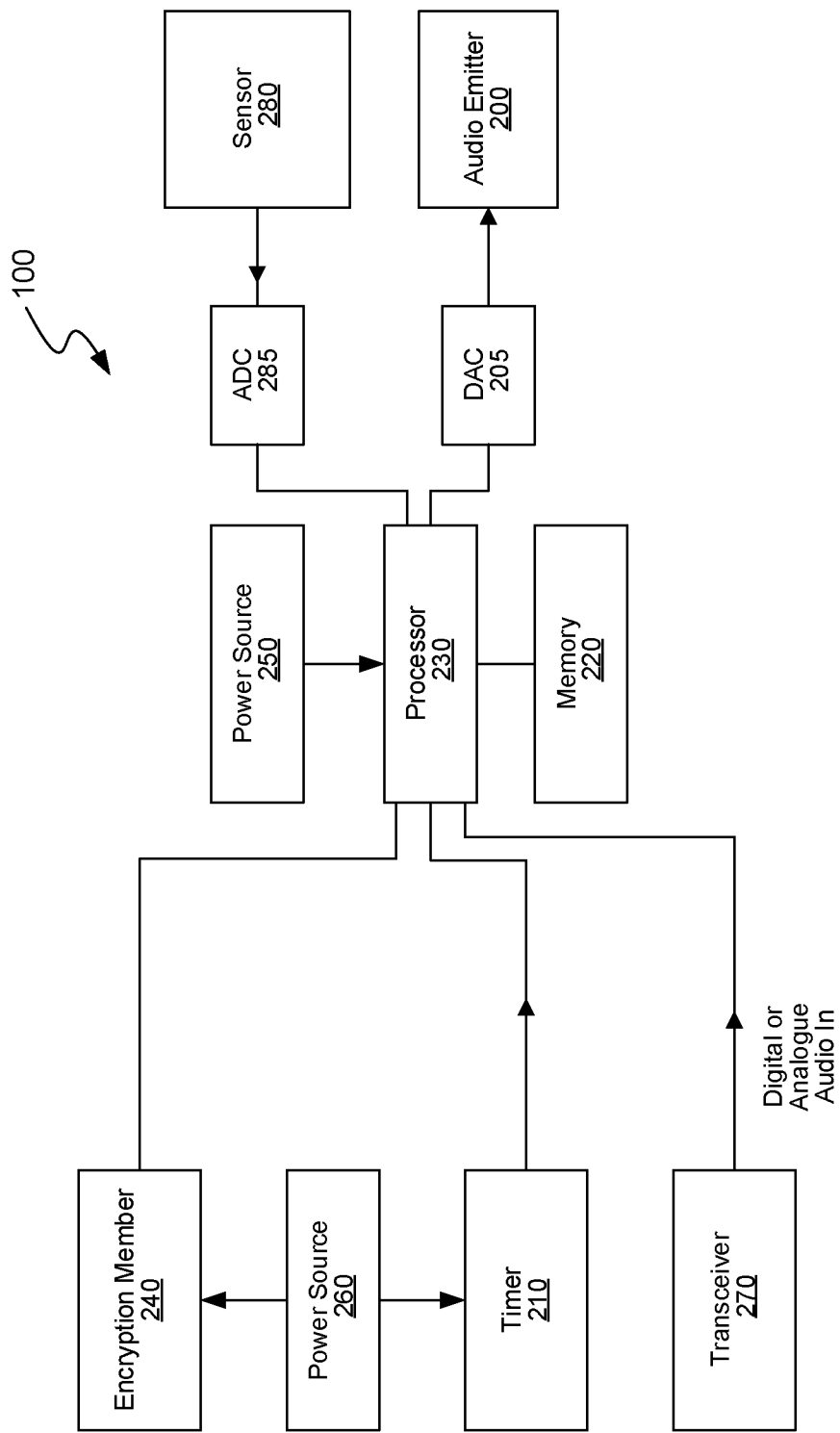
FIG. 2 shows an internal architecture of the audio device.

FIG. 2 shows an internal architecture of the audio device 100. The audio device 100 can be a headphone as shown in FIGS. 1A-1B, a hearing aid, an earphone, an earbud, an Air Pod, etc. The headphone 100 can include an audio emitter 200, a digital-to-analog converter (DAC) 205, a timer 210, a memory 220, a processor 230, an optional encryption member 240, two power sources 250, 260, a transceiver 270, a sensor 280, and an analog-to-digital converter (ADC) 285. To enable addition of the components such as the timer 210 and the encryption member 240 to the headphone 100, the timer 210 and the encryption member 240 can be designed to consume a low amount of power, or to have a power source 260 in addition to the power source 250.

The audio emitter 200 can emit an audio to the user, such as music, podcasts, audiobooks, etc. The audio emitter 200 can include one or more speakers such as a low-frequency speaker and/or a high-frequency speaker. The audio emitter 200 can receive the audio from the DAC 205, which converts the digital signal from the processor 230 to an analog signal for the audio emitter 200 to emit.

The timer 210 can measure an amount of time the audio emitter is emitting an audio. The timer 210 can be a real time clock in the form of an integrated circuit, which can measure current time.

The memory 220 can store an amount of time allocated to a user identification (ID) and a unique encryption key associated with the headphone. The data stored in the memory 220 can be encrypted using the unique encryption key. The amount of time allocated to a user ID can indicate an amount of time that the user is allowed to use the headphone 100. If the user listens to the audio emitted by the headphone 100, the amount of time allocated to the user ID can be decreased by the amount of time measured by the timer 210. Alternatively, the memory 220 can store a counter representing a total amount of time the user has listened to the audio through the headphone 100. The counter can be increased as the amount of time measured by the timer 210 is increased.

The processor 230 can receive an encrypted user ID encrypted with the unique encryption key and retrieve an encrypted amount of time allocated to the user ID encrypted with the unique encryption key. The processor can decrypt the encrypted user ID and the encrypted amount of time and based on the amount of time allocated to the user ID, determine whether to emit the audio. For example, if the amount of time allocated to the user ID is decreased by the amount of time measured by the timer 210, and the amount of time allocated to the user ID is equal to 0 or less, the processor can prevent the audio emitter 200 from emitting the audio. In another example, if the counter representing the total amount of time the user has listened to the audio is increased by the amount of time measured by the timer 210, and the counter is equal to or greater than the amount of time allocated to the user ID, the processor can prevent the audio emitter 200 from emitting the audio.

The headphone 100 can be used without the mobile device 110 or the server 120 in FIG. 1A, by, for example, connecting an analog cable between the headphone 100 and an audio source. Even in that case, the timer 210 can continue measuring the amount of time that the audio emitter is emitting an audio and can update the amount of time allocated to the user ID and/or the counter because the timer 210, the memory 220, and the processor 230 can operate without communicating to the mobile device 110 and the server 120. When the total amount of time the user has listened to the headphone 100 exceeds the amount of time allocated to the user ID, the headphone 100 can stop operating, until the user acquires more time.

The encryption member 240 can encrypt communications between the timer, the memory, and the processor using the unique encryption key. The encryption member 240 can encrypt BIOS communication between the timer 210, the memory 220, the processor 230 and other components of the headphone 100. The encryption member 240 can encrypt communication between the headphone 100 and the mobile device 110 in FIGS. 1A-1B, and the server 120 in FIG. 1A.

Encrypting BIOS communications within the headphone 100 and the communications between the headphone 100 and the mobile device 110 in FIGS. 1A-1B, and the server 120 in FIG. 1A, can prevent tampering with the headphone 100 by changing the user's subscription information, such as increasing or decreasing the amount of time allocated to the user ID, or by obtaining information about the user ID. For example, if the user submits credit card information to obtain more time allocated to the user ID, the encryption member 240 can encrypt the credit card information using the unique encryption key. Encrypted communication also can prevent third-party applications from obtaining information from the headphone 100, thus decreasing the likelihood that third-party applications can tamper with information contained within the headphone 100.

The transceiver 270 can be wired or wireless. The transceiver 270 can communicate with the mobile device 110 and the server 120, through communication channels 130, 140 in FIGS. 1A-1B. The transceiver 270 can enable the headphone 100 to be regularly connected to the Internet. The transceiver 270 can communicate using Internet protocols; cellular network protocols; local area network protocols; mesh network protocols; peer-to-peer network protocols; satellite protocol; or short range wireless protocols, such as Bluetooth, Wi-Fi, infrared, near field communication, ultraband and ZigBee, etc., as described in this application. For example, the transceiver 270 can communicate using a dual-mode Bluetooth protocol enabling audio and data transmission.

The sensor 280 can measure a perceived frequency and a perceived amplitude based on a received frequency and a received amplitude emitted by the audio emitter. The sensor 280 can be a microphone or a dry electrode measuring an optoacoustic emission or an auditory evoked potential. The sensor 280 can provide an analog input to the ADC 285, which converts the analog input to a digital input and sends the digital input to the processor 230 for processing.

Based on the perceived frequency and the perceived amplitude generated in response to the received frequency and the received amplitude, the processor 230 can create a user profile, which is unique to the particular user. The processor can then identify the user based on the hearing profile. For example, the processor can measure the current hearing profile of the user and can match the hearing profile to a previously obtained hearing profile. Because the hearing profile is unique to the user and is personally identifiable information, the hearing profile can be encrypted using the encryption member 240, to prevent third parties from obtaining the hearing profile. The hearing profile is an example of a new data that can be obtained while the user is using the audio device.

The processor 230 can determine whether the amount of time allocated to the user ID authorizes the user ID to receive the audio. When the amount of time allocated to the user ID does not authorize the user to receive the audio, the processor 230 can prevent the audio emitter from emitting the audio. When the amount of time allocated to the user ID does authorize the user to receive audio, the processor 230 can send an instruction to the audio emitter 200 to continue emitting the audio.

The processor 230 can allow the user to update the amount of time allocated to the user ID. For example, the processor 230 can receive an updated amount of time allocated to the user ID greater than the amount of time allocated to the user ID. For example, the user can buy additional time on the headphone 100. Upon determining that the updated amount of time allocated to the user ID authorizes the user ID to receive the audio, the processor 230 can send an instruction to the audio emitter to emit the audio.

The processor 230 can determine whether the amount of time allocated to the user ID is within a predetermined amount of time, such as several weeks, and can send an instruction, encrypted by the unique encryption key, to the audio emitter to emit an audio informing the user about the amount of time allocated to the user ID. For example, the processor 230 can determine that the user has two weeks of headphone 100 use left. The processor 230 can construct the audio emitter to play a message to the user informing the user that the user has only two weeks of headphone use left.

Figure 3:
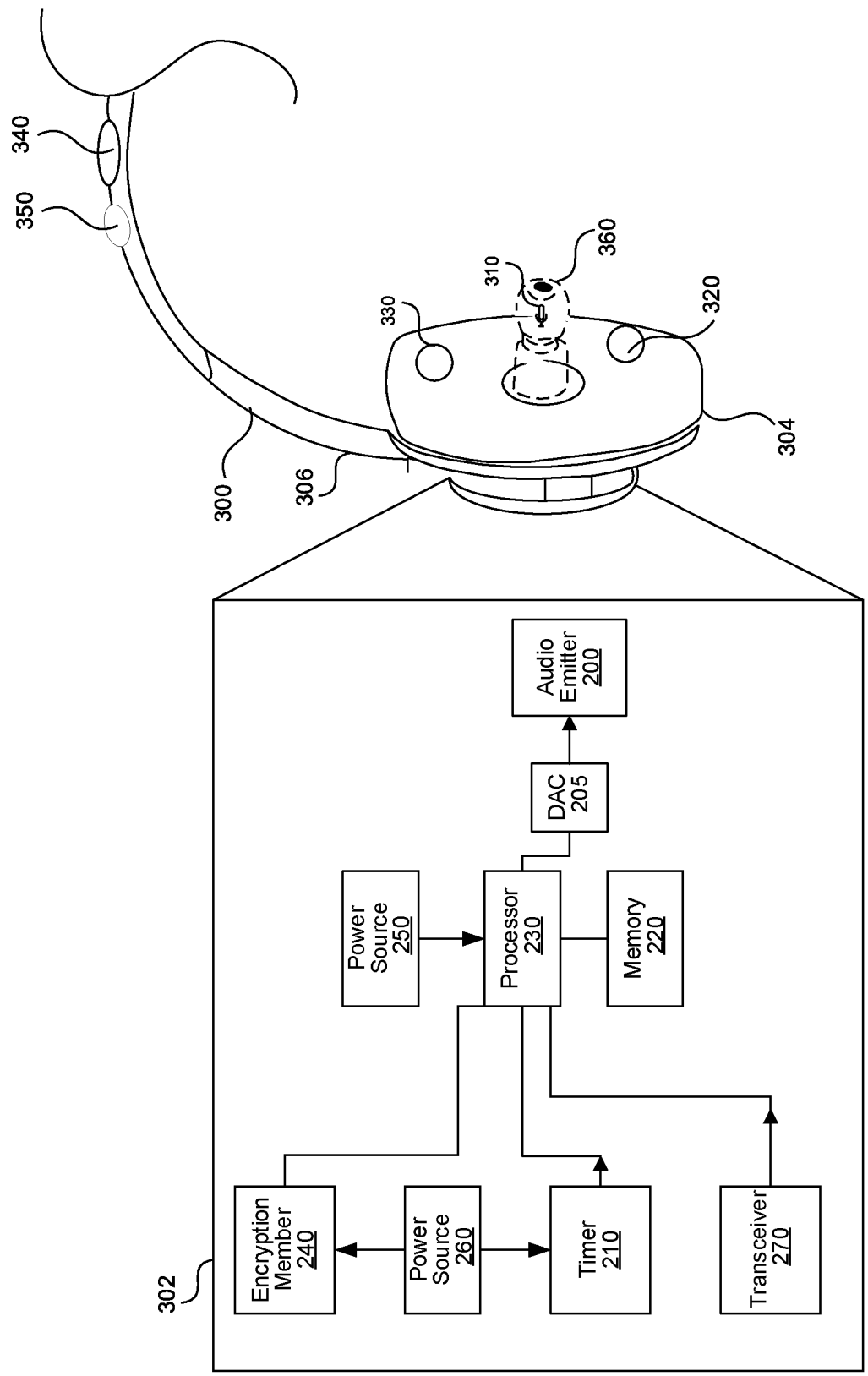
FIG. 3 shows an internal structure of the audio device with sensors.

FIG. 3 shows an internal structure of the audio device with sensors. The audio device 300 can have one or more sensors such as 310, 320, 330, 340, 350 to measure how the user of the audio device 300 perceives sound. The audio device 300 can be a headphone, as shown in FIG. 3, a hearing aid, an earbud, an Air Pod, etc. The circuitry 302 can be a part of the audio device 300, such as a part of the earcup 304.

The sensor 310 can be a microphone enclosed within an earbud 360 and placed within a user's ear canal. The sensor 310 can measure optoacoustic emissions generated in the user's cochlea in response to an audio played by the audio emitter 200. In other words, the sensor 310 measures a perceived frequency and a perceived amplitude generated in response to a received frequency and a received amplitude contained in the audio played by the audio emitter 200.

The sensors 320, 340 can be capacitive sensors, and sensors 330, 350 can be dry electrodes. The sensors 320, 330, 340, 350 can be disposed anywhere on the audio device 300 as long as the sensors 320, 330, 340, 350 are in contact with the user's skin. For example, the sensors 320, 330, 340, 350 can be disposed on the earcup 304, on the headband 306, or on the earbud 360. The sensors 320, 330, 340, 350 can measure auditory evoked potentials generated by the user's skin in response to an auditory stimulus applied to one or both of the user's ears through the audio device 300.

Figure 4:
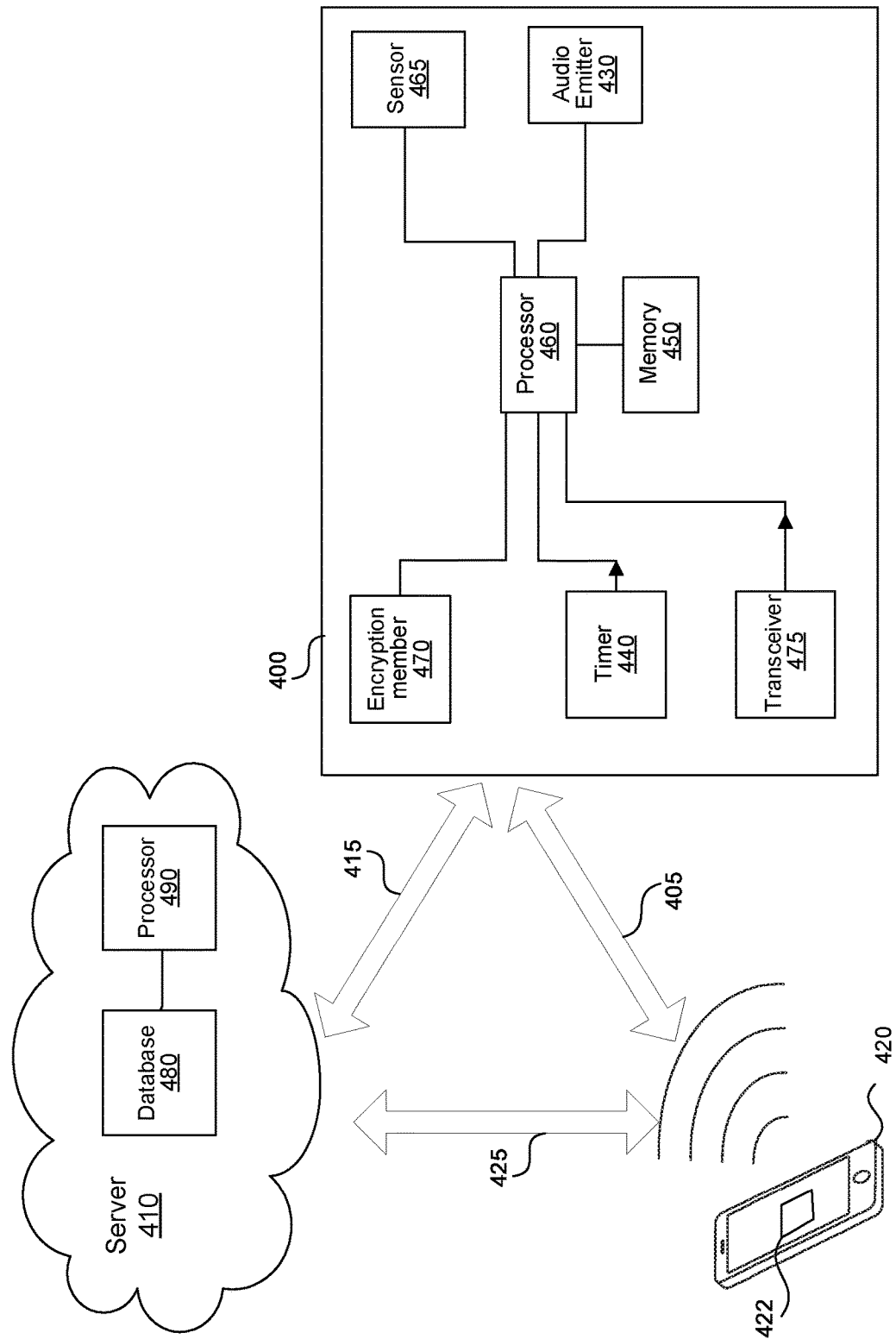
FIG. 4 shows internal components of a system including an audio device with timing capabilities and enhanced security.

FIG. 4 shows internal components of a system including an audio device with timing capabilities and enhanced security. The system can include an audio device 400, a server 410, and a mobile device 420, communicating over channels 405, 415, 425, as described in this application.

The audio device 400 can be a headphone, a hearing aid, an earbud, an Air Pod, etc. The audio device 400 can include an audio emitter 430, a timer 440, a memory 450, a processor 460, a sensor 465, the encryption member 470 and the transceiver 475. The server 410 can include a database 480 and a processor 490. The mobile device 420 can include a processor 422. The mobile device 420 can be a cell phone, a personal digital assistant, a tablet, a watch, smart glasses, etc.

The audio emitter 430 can emit an audio. The timer 440 can measure an amount of time the audio emitter 430 is emitting an audio. The timer 440 can pass the measured amount of time to at least one of the processors 460, 490. The memory 450 can store a unique encryption key associated with the audio device 400. The transceiver 475 can be used to communicate with the server 410 and the mobile device 420 through communication channels 405, 415, as described in this application.

The processor 460 can obtain a user ID and can send the user ID to a second processor. The processor 460 can receive the measured amount of time from the timer 440, obtain an amount of time allocated to the user ID, and determine whether the user ID is entitled to listen to an audio.

The encryption member 470 can encrypt a communication between the timer, the memory, and the processors 460, 490, etc. using the unique encryption key. Encryption of communication prevents eavesdropping of confidential information such as the amount of time allocated to the user ID, personally identifiable information such as hearing profile, credit card information, etc.

The database 480 can store an amount of time allocated to the user ID. The amount of time allocated to the user can be decremented by the measured amount of time or can be constant and the usage time can be incremented. The usage time can represent the amount of time that the user has used the audio device 400. When the usage time is equal to or greater than the time allocated to the user, the audio device can stop emitting the audio.

The user ID can have a certain amount of time per audio device 400, or per category of audio devices. For example, the category of audio devices can include "share," "own," "rent." Devices that fall into the category "share" and "rent," can be shared among multiple users. So, if the user ID has an amount of time allocated to the user ID that is greater than zero, the user ID can use any of the devices in the category "share" and "rent" to listen to the music. The amount of time allocated to the user can be decremented by the amount of time the user has listened to any of the audio devices in the "share" and "rent" category. The decremented amount of time can be stored in the database 480, so that the database 480 keeps track of the remaining time associated with the user ID.

The processor 490 can receive the user ID encrypted with the unique encryption key, decrypt the encrypted user ID, retrieve the amount of time allocated to the user ID from the database 480, and based on the amount of time allocated to the user ID on the unique audio device ID, determine whether to emit the audio.

For example, if the amount of time allocated to the user ID is decremented by the amount of time the user uses the audio device 400, the processor 490 can check whether the amount of time is positive. If the amount of time is positive, the processor 490 can permit the audio device 400 to emit the audio. In another example, if the amount of time allocated to the user ID is kept constant, and usage time tracks the amount of time the user ID listens to the audio, the processor 490 can compare the amount of time allocated to the user in the usage time, and if the usage time is equal to or exceeds the amount of time allocated to the user, the processor 490 can prevent the audio device from emitting the audio.

In one embodiment, the system can enable the user to use a category of audio devices. The categories can include "share," "own," and "rent," and the audio devices can be any combination of headphones, hearing aids, earbuds, Air Pods, etc. For example, the amount of time allocated to the user ID can be one month, which can enable the user to use a hearing aid, an earbud, and an air phone, all of which are categorized as either share or rent.

In this embodiment, the memory 450 can store a unique audio device identification (ID) associated with the audio device 400. The unique audio device ID ca uniquely identify the audio device 400 among all other audio devices. In addition to storing the unique audio device ID in the memory 450 of the audio device 400, the audio device ID can be encoded on a barcode on a delivery box. The database 480 can store one or more unique audio device IDs enabled to provide a timed service and an amount of time allocated to the user ID. The one or more unique audio device IDs can be a list of all the audio devices categorized as "share" and/or "rent."

The amount of time allocated to the user ID can be stored in the memory 450 and/or the database 480. As explained in this application, the amount of time allocated to the user can be a counter that is decremented or can be constant and the usage time can be incremented. The usage time is a new data generated based on the measured time using the timer 440.

The processor 460, 490 can receive the unique audio device ID encrypted with the unique encryption key, decrypt the unique audio device ID, determine whether the unique audio device ID is part of the one or more unique audio device IDs enabled to provide the timed service, retrieve the amount of time allocated to the user ID, and when the unique audio device ID is part of the one or more unique audio device IDs, determine whether to emit the audio based on the amount of time allocated to the user. If the amount of time allocated to the user ID is exhausted while the audio emitter 430 is emitting an audio, the audio emitter 430 can stop emitting the audio without completing the audio emission.

The processor 422 associated with the mobile device 420 can authenticate the user. The processor 422 can receive the user ID from the user and the unique audio device ID from the memory 450 associated with the audio device 400. The processor 422 can check whether the user ID is permitted access to the audio device 400 associated with the unique audio device ID. When the user ID is permitted access to the audio device 400, the processor 422 can authenticate the user, enable the user to access the audio device, and receive a request from the user to emit the audio.

To check whether the user ID is permitted access, the processor 422 can encrypt the user ID and the unique audio device ID with the unique encryption key, send the encrypted user ID and the encrypted unique audio device ID to the processor 490, and receive a message from the processor 490 whether the user ID is associated with the audio device ID in the database. The database 480 can link the unique audio device ID with an email address used when the audio device 400 was purchased. The email address can be the user ID, or can be associated with the user ID. Whenever the audio device 400 connects to a software application running on the processor 422, the processor 422 can ask the processor 490 to check if the unique audio device ID and the user ID match. If the unique audio device ID is associated with the appropriate categories such as "own" or "rent," and the user ID matches the unique audio device ID, then the processor 490 can check if the amount of time allocated to the user ID permits the user to use the audio device, for example, whether the amount of time allocated to the user is greater than the usage time counter. If so, the processor 490 can communicate to the processor 460 to increase a usage time counter by another month or until the end of another billing period. The usage time counter can represent the amount of time the user has access to the audio device 400.

The processor 460, 490 can determine whether the amount of time allocated to the user ID authorizes the user ID to receive the audio. When the amount of time allocated to the user ID does not authorize the user to receive the audio, the processor 460, 490 can prevent the audio emitter from emitting the audio. Conversely, when the amount of time allocated to the user ID does authorize the user to receive the audio, the processor 460, 490 can enable the audio to emit the audio.

The processor 460, 490 can allow the user to increase the amount of time allocated to the user ID. The processor 460, 490 can receive an updated amount of time allocated to the user ID. The updated amount of time can be greater than the amount of time allocated to the user ID. For example, the user can pay to increase the amount of time allocated to the user ID. Upon determining that the updated amount of time allocated to the user ID authorizes the user ID to receive the audio, the processor 460, 490 can permit the audio emitter to emit the audio.

The processor 460, 490 can provide updates to the user about the time remaining to the user ID. The processor 460, 490 can determine whether the amount of time allocated to the user ID is within a predetermined amount of time. For example, the processor 460, 490 can determine that the time remaining to the user ID is about two weeks. When the time remaining is approximately two weeks, the processor 460, 490 can send an instruction, encrypted by the unique encryption key, to the audio emitter 430 to emit an audio informing the user about the amount of time allocated to the user ID.

The sensor 465 can be a microphone, a dry electrode, a capacitive sensor, etc., as described in this application. The sensor 465 can measure a perceived frequency and a perceived amplitude generated in response to a received frequency and a received amplitude emitted by the audio emitter. The processor 460, 490 can create a user profile correlating the perceived frequency and amplitude to the received frequency and amplitude. Based on the user profile, the processor 460, 490 can identify the user by comparing the measured hearing profile to multiple hearing profiles stored in the memory 450 or the database 480. The stored hearing profiles can be associated with a corresponding user ID. Since the hearing profile is unique to each user, once the processor 460, 490 finds a match between the measured hearing profile and the stored hearing profile, the processor 460, 490 can identify the user by retrieving the user ID associated with the stored hearing profile.

Figure 5:
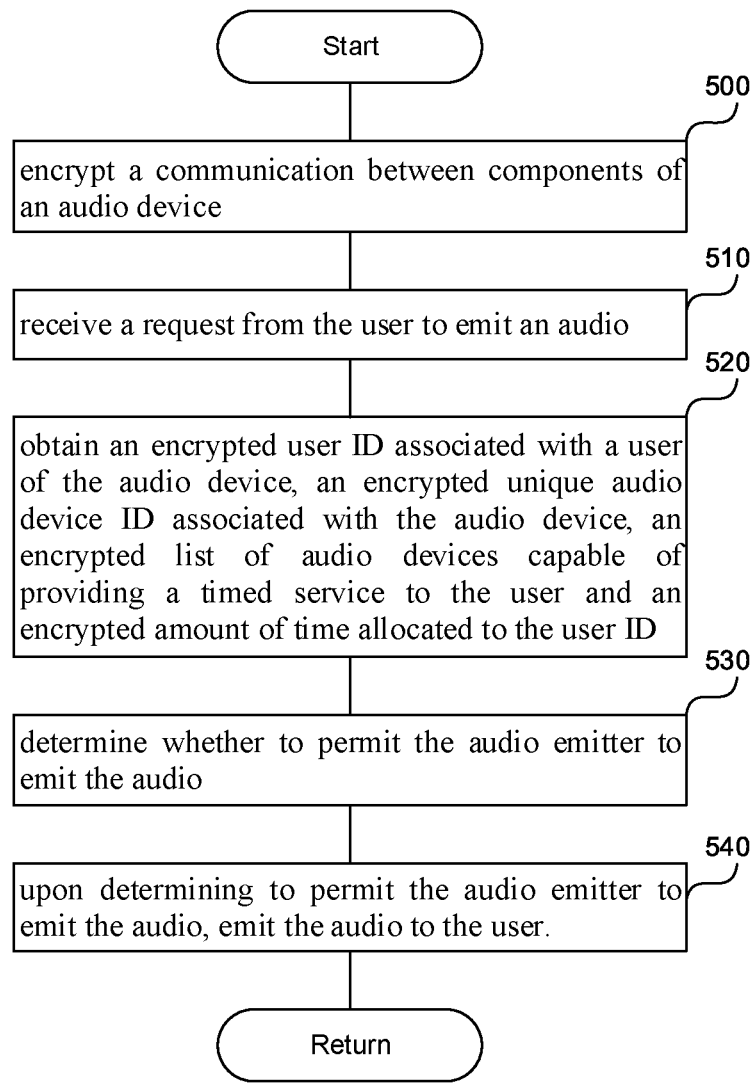
FIG. 5 is a flowchart of a method to determine whether to permit an audio device to emit an audio.

FIG. 5 is a flowchart of a method to determine whether to permit an audio device to emit an audio. In step 500, to preserve security of communication between audio device components and to enable the audio device to store secure information, a processor and/or an encryption member can encrypt a communication between components of an audio device by using a unique encryption key stored in a memory of an audio device. The secure information can include an amount of time allocated to a user ID enabling the user ID to use the audio device by, for example, listening to music. The secure information can also include a hearing profile that ca uniquely identify the user. In step 510, the processor can receive a request from the user to emit an audio through an audio emitter of the audio device.

In step 520, the processor can obtain an encrypted user ID associated with a user of the audio device, an encrypted unique audio device ID associated with the audio device, an encrypted list of unique audio device IDs capable of providing a timed service to the user and an encrypted amount of time allocated to the user ID. The user ID, the unique audio device ID, the list of unique audio device IDs capable of providing the timed service to the user and the amount of time allocated to the user ID can be encrypted with the unique encryption key. The unique audio device ID is associated with each audio device and can be stored in the memory of the audio device, as well as in the database, as described in this application. The list of unique audio device IDs capable of providing the timed service can include one or more audio devices, and can be a subset of all audio devices having the unique audio device ID.

In step 530, the processor can determine whether to permit the audio emitter to emit the audio by decrypting encrypted communication, determining that the unique audio device ID is contained in the list of unique audio device IDs configured to provide a timed service to the user, and determining that an amount of time allocated to the user ID has a remaining time to use the audio device.

For example, the unique audio device ID can be any combination of alphanumeric characters such as "193!Aty." The processor can determine that the unique audio device ID "193!Aty" is not in the list of unique audio device IDs that can provide the timed service to the user. After such a determination, the processor can prevent the audio emitter from emitting the audio to the user. The processor can determine that the unique audio device ID is in the list of unique audio device IDs. After such a determination, the processor can determine whether the amount of time allocated to the user ID has any remaining time to use the audio device. To make the determination, the processor can determine whether the time allocated to the user ID is positive, or whether a usage time counter, indicating the time the user has used the audio device, is greater than the amount of time allocated to the user ID. If the amount of time allocated to the user ID doesn't have any remaining time, the processor can prevent the audio device from emitting the audio. If the amount of time allocated to the user ID has remaining time, the processor can allow the audio emitter to emit the audio. In step 540, after the processor determines to permit the audio emitter to emit the audio, the audio emitter can emit the audio to the user.

The timing member can measure an amount of time an audio emitter of the audio device is emitting an audio. The measured amount of time can be subtracted from the amount of time allocated to the user ID, or the usage time counter can be increased by the measured amount of time. When the measured amount of time exceeds the amount of time allocated to the user ID, such as the amount of time allocated to the user ID is 0 or less, or the usage time counter is greater than the amount of time allocated to the user, the processor can prevent the audio emitter from emitting the audio.

The user can increase the amount of time allocated to the user ID by for example paying for additional time, offering a coupon for additional time, winning a contest, etc. The processor can receive an updated amount of time allocated to the user ID. The updated amount of time can be greater than the amount of time allocated to the user ID. Upon determining that the updated amount of time allocated to the user ID authorizes the user ID to receive the audio, the processor can permit the audio emitter to emit the audio.

The processor can create a hearing profile of the user, which uniquely identifies the user. To create the hearing profile, the processor can emit the audio to the user and can measure a perceived frequency and a perceived amplitude generated in response to a received frequency and a received amplitude emitted by the audio emitter. The measurement can be performed by a sensor such as a microphone, a dry electrode and/or a capacitive sensor. The sensor can measure optoacoustic emissions (OAE) or auditory evoked potential (AEP) generated in response to the received frequency and the received amplitude. Based on the OAE and/or AEP, the processor can create the hearing profile indicating how the user perceives the particular frequency of a particular amplitude. For example, the hearing profile can indicate that a received frequency of 10 kHz at 10 dB is perceived as a frequency of 11 kHz at 7 dB.

The hearing profile can be unique to each user. As a result, the processor can identify the user based on the hearing profile by matching the hearing profile to a previously obtained hearing profile associated with a user ID. The previously obtained hearing profile can be stored in the database and associated with the user ID.

In another embodiment, the processor can enable or disable operation of a headphone based on a criterion associated with the headphones. The processor can obtain a value of the criterion associated with the headphone configured to emit an audio, can determine whether the value of the criterion exceeds a predetermined threshold, and when the value of the criterion exceeds a predetermined threshold, the processor can prevent headphone from emitting the audio. The criterion can be time, various permissions associated with the headphones, whether a user ID and headphone ID are compatible, etc. The communication between the processor and other parts of the system, such as a timer, and/or a memory can be encrypted.

When the criterion is time, the memory can store an amount of time allocated to a user ID, and the timer can measure an amount of time the headphones have played the audio to the user ID. The processor can receive the user ID, retrieve the amount of time allocated to the user ID from the database, and based on the amount of time allocated to the user ID determine whether to emit the audio. For example, when the total amount of time the headphones have played the audio to the user exceeds the allocated amount of time, the processor can prevent the headphones from playing the audio. The processor can receive an updated amount of time allocated to the user ID greater than the amount of time allocated to the user ID, for example, when the user associated with the user ID buys additional time for the headphones. The processor, upon determining that the updated amount of time allocated to the user ID authorizes the user ID to receive the audio, the processor can permit the headphone to emit the audio.

When the criterion is permissions associated with the headphone, the memory can store a unique headphone identification (ID) associated with the headphone, and one or more unique headphone IDs that are subject to the criterion, such as headphones enabled to provide a timed service, headphones subject to emit audio during a predetermined time period, headphones subject to emit at the predetermined location, etc.

In one example, the headphones can be subject to the criterion of emitting audio during a specified time of day, such as 8 AM-5 PM. When the current time is outside of the specified time range, the processor can present the headphones from emitting the audio. The processor can receive the unique headphone ID, determine whether the unique headphone ID is part of the one or more unique headphone IDs subject to the criterion of emitting audio during the specified time of day. When the unique headphone ID is part of the one or more unique headphone IDs, the processor can determine whether to emit the audio based on the current time and the specified time range.

In another example, the headphones can be subject to the criterion of emitting audio only in predetermined locations. The location can be a geographical location, or can be an Internet location. In a more specific example, the headphones, can be permitted to work only in the U.S. The headphone location can be determined using a GPS locator. When the headphone is outside of the geographical location, the processor can disable the headphones. In other specific example, the headphones can be enabled to emit audio only when the headphones are connected to a predetermined local area network.

In a third example, the headphones can be subject to the criterion of providing a timed service. The memory can further store the amount of time allocated to the user ID. The processor can receive the unique headphone ID, determine whether the unique headphone ID is part of the one or more unique headphone IDs enabled to provide the timed service, retrieve the amount of time allocated to the user ID, and when the unique headphone ID is part of the one or more unique headphone IDs, determine whether to emit the audio based on the amount of time allocated to the user ID.

When the criterion is whether a user ID and headphone ID are compatible, the processor can receive the user ID from a user and a unique headphone ID from the memory associated with the headphone. The processor can check whether the user ID is permitted access to the headphone associated with the unique headphone ID. When the user ID is permitted access to the headphone associated with the unique headphone ID, the processor can enable the user to access the headphone.

Computer

Figure 6:
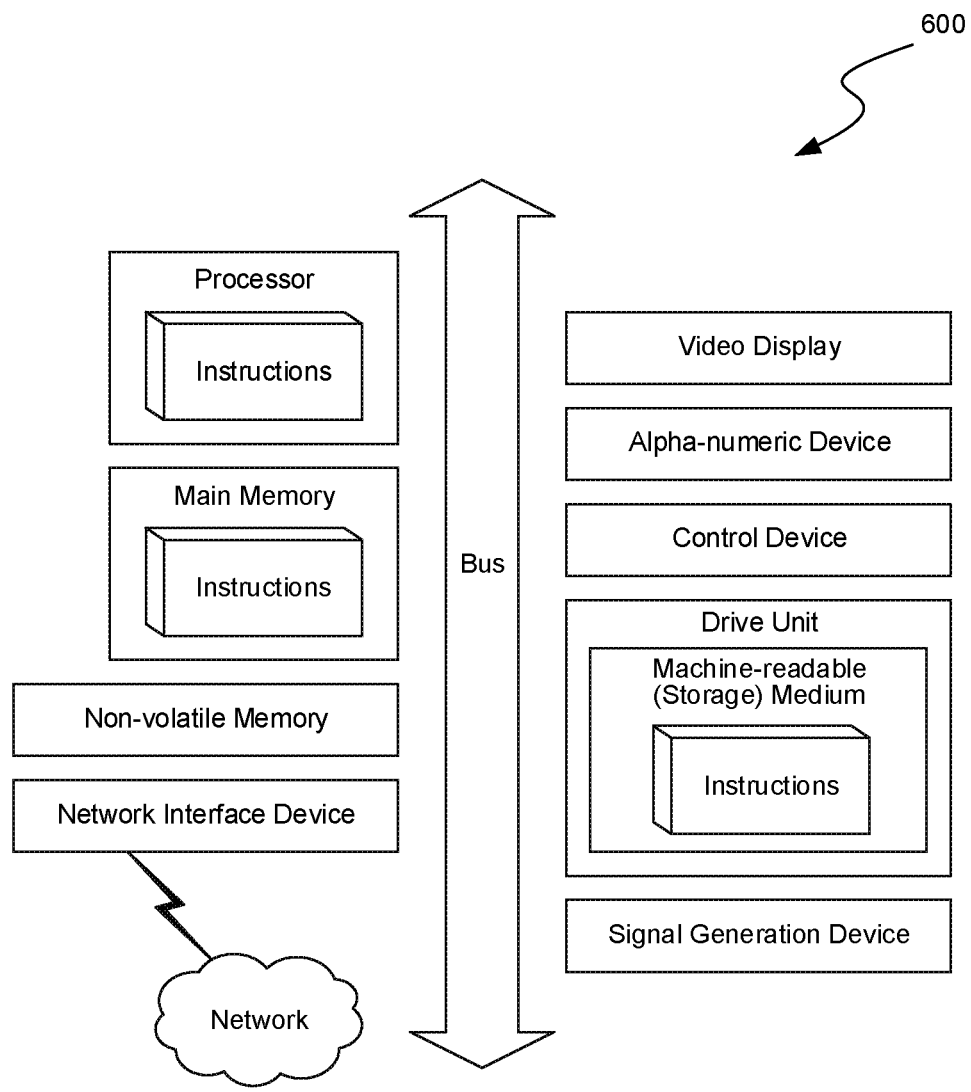
FIG. 6 is a diagrammatic representation of a machine in the example form of a computer system within which a set of instructions, for causing the machine to perform any one or more of the methodologies or modules discussed herein, may be executed.

FIG. 6 is a diagrammatic representation of a machine in the example form of a computer system 600 within which a set of instructions, for causing the machine to perform any one or more of the methodologies or modules discussed herein, may be executed.

In the example of FIG. 6, the computer system 600 includes a processor, memory, non-volatile memory, and an interface device. Various common components (e.g., cache memory) are omitted for illustrative simplicity. The computer system 600 is intended to illustrate a hardware device on which any of the components described in the example of FIGS. 1-5 (and any other components described in this specification) can be implemented. The computer system 600 can be of any applicable known or convenient type. The components of the computer system 600 can be coupled together via a bus or through some other known or convenient device.

The computer system 600 can be associated with the audio device 100 in FIGS. 1A-1B, the mobile device 110 in FIGS. 1A-1B, and or the server 120 in FIG. 1A. The processor of the computer system 600 can perform any of the methods described in this application. For example, the processor of the computer system 600 can determine whether the audio device 100 is permitted to emit an audio. The nonvolatile memory, the main memory and/or the drive unit of the computer system 600 can store various data as described in this application such as the user ID, the unique audio device ID, the encryption key, the list of unique audio device IDs capable of providing timed service, etc. The network of the computer system 600 can be the network 130, 140, 150 in FIG. 1A.

This disclosure contemplates the computer system 600 taking any suitable physical form. As example and not by way of limitation, computer system 600 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 600 may include one or more computer systems 600; be unitary or distributed; span multiple locations; span multiple machines; or reside in a cloud, which may include one or more cloud components in one or more networks. Where appropriate, one or more computer systems 600 may perform without substantial spatial or temporal limitation one or more steps of one or more methods described or illustrated herein. As an example and not by way of limitation, one or more computer systems 600 may perform in real time or in batch mode one or more steps of one or more methods described or illustrated herein. One or more computer systems 600 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 600. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing an entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 600. The interface can include an analog modem, ISDN modem, cable modem, token ring interface, satellite transmission interface (e.g. "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 6 reside in the interface.

In operation, the computer system 600 can be controlled by operating system software that includes a file management system, such as a disk operating system. One example of operating system software with associated file management system software is the family of operating systems known as Windows® from Microsoft Corporation of Redmond, Washington, and its associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD-ROMS), Digital Versatile Discs, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list in which a change in state for a binary one to a binary zero or vice-versa in a memory device may comprise a transformation, such as a physical transformation. Rather, the foregoing are intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A headphone comprising:
an audio emitter configured to emit an audio;
a sensor configured to measure a perceived frequency and a perceived amplitude based on a received frequency and a received amplitude emitted by the audio emitter;
a timer configured to measure an amount of time the audio emitter is emitting the audio;
a memory configured to store a user hearing profile and an amount of time allocated to the user hearing profile; and
a processor configured to:
receive information from the sensor, the information comprising a measurement of the perceived frequency and the perceived amplitude based on a measurement of the received frequency and the received amplitude;
determine the user hearing profile based on information received by the sensor, the user hearing profile correlating the measurement of the received frequency and the received amplitude to the measurement of the perceived frequency and the perceived amplitude;
retrieve the amount of time allocated to the user hearing profile; and
based on the amount of time allocated to the user hearing profile, determine whether to emit the audio.

2. The headphone of claim 1, wherein the processor is further configured to:
determine whether the amount of time allocated to the user hearing profile authorizes the user hearing profile to receive the audio; and
when the amount of time allocated to the user hearing profile does not authorize the user hearing profile to receive the audio, prevent the audio emitter from emitting the audio.

3. The headphone of claim 2, wherein the processor is further configured to:
receive an updated amount of time allocated to the user hearing profile MD greater than the amount of time allocated to the user hearing profile; and
upon determining that the updated amount of time allocated to the user hearing profile authorizes the user hearing profile to receive the audio, send an instruction to the audio emitter to emit the audio.

4. The headphone of claim 1, wherein the processor is further configured to:
determine whether the amount of time allocated to the user hearing profile is within a predetermined amount of time; and
send an instruction to the audio emitter to emit the audio providing information about the amount of time allocated to the user hearing profile.

5. The headphone of claim 1, further comprising:
wherein the memory is further configured to store a unique encryption key; and
wherein the processor is further configured to:
receive an encrypted user hearing profile encrypted with the unique encryption key, retrieve an encrypted amount of time allocated to the user hearing profile encrypted with the unique encryption key, decrypt the encrypted user hearing profile and the encrypted amount of time, and based on the amount of time allocated to the user hearing profile, determine whether to emit the audio.

6. The headphone of claim 1, further comprising:
an encryption member to encrypt a communication between the timer, the memory, and the processor using a unique encryption key.

7. A system comprising:
a sensor configured to measure a perceived frequency and a perceived amplitude based on a received frequency and a received amplitude emitted by an audio device;
a memory storing instructions and a user hearing profile, wherein the user hearing profile comprises an amount of time allocated to the user hearing profile; and
a processor configured by the instructions to:
receive information from the sensor, the information comprising a measurement of the perceived frequency and the perceived amplitude based on a measurement of the received frequency and a received amplitude;
determine the user hearing profile based on information received by the sensor, the user hearing profile correlating the measurement of the received frequency and the received amplitude to the measurement of the perceived frequency and the perceived amplitude;
based on the determined user hearing profile, obtain a value of a criterion associated with an audio device configured to emit an audio;
determine whether the value of the criterion exceeds a predetermined threshold; and
when the value of the criterion exceeds the predetermined threshold, prevent the audio device from emitting the audio.

8. The system of claim 7, further comprising:
a timer configured to measure an amount of time the audio device is emitting the audio;
wherein the memory is further configured to store an amount of time allocated to a user hearing profile; and
wherein the processor is further configured to:
in response to receiving the user hearing profile, determine whether the value of the criterion exceeds the predetermined threshold; and
retrieve the amount of time allocated to the user hearing profile from the memory, and based on the amount of time allocated to the user hearing profile determine whether to emit the audio.

9. The system of claim 7, further comprising:
wherein the memory is further configured to store one or more unique audio device IDs, wherein the one or more unique audio device IDs are associated with the audio device, and wherein at least one unique audio device ID is enabled to provide a timed service and an amount of time allocated to a user hearing profile;
wherein the processor is further configured to:
receive the at least one unique audio device ID;
determine whether the at least one unique audio device ID is part of the one or more unique audio device IDs enabled to provide the timed service; and retrieve the amount of time allocated to the user hearing profile, and when the at least one unique audio device ID is part of the one or more unique audio device IDs, determine whether to emit the audio based on the amount of time allocated to the user hearing profile.

10. The system of claim 7, wherein the processor is further configured to:
receive the user hearing profile from a user and a unique audio device ID from the memory associated with the audio device;
check whether the user hearing profile is permitted access to the audio device associated with the unique audio device ID; and
when the user hearing profile is permitted access to the audio device associated with the unique audio device ID, enable the user to access the audio device.

11. The system of claim 7, wherein the processor is further configured to:
determine whether an amount of time allocated to the user hearing profile authorizes the user hearing profile to receive the audio; and
when the amount of time allocated to the user hearing profile does not authorize the user hearing profile to receive the audio, prevent the audio device from emitting the audio.

12. The system of claim 7, wherein the processor is further configured to:
receive an updated amount of time allocated to the user hearing profile greater than an amount of time allocated to the user hearing profile; and
upon determining that the updated amount of time allocated to the user hearing profile authorizes the user hearing profile to receive the audio, permitting the audio device to emit the audio.

13. The system of claim 7, wherein the processor is further configured to:
determine whether an amount of time allocated to the user hearing profile is within a predetermined amount of time; and
send an instruction to the audio device to emit the audio providing information about the amount of time allocated to the user hearing profile.

14. The system of claim 7, further comprising:
wherein the memory is further configured to store a unique encryption key; and
an encryption member configured to encrypt a communication between the memory, and the processor using the unique encryption key.

15. A method comprising:
receiving a request from a user to emit an audio through an audio emitter of an audio device;
obtaining a user hearing profile associated with the user of the audio device, wherein the user hearing profile correlates a received frequency and a received amplitude to a perceived frequency and a perceived amplitude of the user;
obtaining a unique audio device ID associated with the audio device, a list of unique audio device IDs configured to provide a timed service to the user and an amount of time allocated to the user hearing profile;
determining whether to permit the audio emitter to emit the audio by determining that the unique audio device ID is included in the list of unique audio device IDs configured to provide the timed service to the user, and determining that the amount of time allocated to the user hearing profile has a remaining time to use the audio device; and
upon determining to permit the audio emitter to emit the audio, emitting the audio to the user.

16. The method of claim 15, further comprising:
encrypting a communication between components of the audio device by using a unique encryption key stored in a memory of the audio device;
wherein obtaining the user hearing profile further comprises:
obtaining secure data encrypted with the unique encryption key, wherein the secure data comprises an encrypted user hearing profile associated with the user of the audio device, an encrypted unique audio device ID associated with the audio device, an encrypted list of unique audio device IDs configured to provide the timed service to the user and an encrypted amount of time allocated to the user hearing profile; and
determining whether to permit the audio emitter to emit the audio by decrypting the encrypted communication.

17. The method of claim 15, further comprising:
measuring an amount of time the audio emitter of the audio device is emitting the audio; and
when the measured amount of time exceeds the amount of time allocated to the user hearing profile, preventing the audio emitter from emitting the audio.

18. The method of claim 15, further comprising:
receiving an updated amount of time allocated to the user hearing profile greater than the amount of time allocated to the user hearing profile; and
upon determining that the updated amount of time allocated to the user hearing profile authorizes the user hearing profile to receive the audio, permitting the audio emitter to emit the audio.

19. The headphone of claim 1, wherein the processor is further configured to identify a user based on the user hearing profile.

* * * * *

UNITED STATES PATENT AND TRADEMARK OFFICE
CERTIFICATE OF CORRECTION

| | | |
|---|---|---|
| PATENT NO. | : 11,995,201 B2 | Page 1 of 1 |
| APPLICATION NO. | : 17/411934 | |
| DATED | : May 28, 2024 | |
| INVENTOR(S) | : Luke John Campbell et al. | |

It is certified that error appears in the above-identified patent and that said Letters Patent is hereby corrected as shown below:

In the Specification

In Column 1, Line 39, delete "ca" and insert --can--.

In Column 3, Line 23, delete "ca" and insert --can--.

In Column 3, Line 46, delete "ca" and insert --can--.

In Column 3, Line 49, delete "ca" and insert --can--.

In Column 5, Line 53, delete "optoacoustic" and insert --otoacoustic--.

In Column 6, Line 42, delete "optoacoustic" and insert --otoacoustic--.

In Column 8, Line 11, delete "ca" and insert --can--.

In Column 9, Line 65, delete "ca" and insert --can--.

In Column 11, Line 7, delete "optoacoustic" and insert --otoacoustic--.

In Column 12, Line 59, delete "and or" and insert --and/or--.

In the Claims

In Column 17, Claim 3, Line 54, delete "profile MD" and insert --profile--.

Signed and Sealed this
Twenty-second Day of October, 2024

Katherine Kelly Vidal
*Director of the United States Patent and Trademark Office*